US010240119B2

(12) United States Patent
Bradin et al.

(10) Patent No.: US 10,240,119 B2
(45) Date of Patent: Mar. 26, 2019

(54) COMBINED ANAEROBIC DIGESTER AND GTL SYSTEM AND METHOD OF USE THEREOF

(71) Applicant: Maverick Biofuels, Inc., RTP, NC (US)

(72) Inventors: David Bradin, Chapel Hill, NC (US); Samuel Yenne, Raleigh, NC (US); Eric Cumming, Raleigh, NC (US); Jeffrey Harrison, Hammonton, NJ (US)

(73) Assignee: Maverick Biofeuls, Inc, RTP, NC (US)

( * ) Notice: Subject to any disclaimer, the term of this patent is extended or adjusted under 35 U.S.C. 154(b) by 0 days.

(21) Appl. No.: 15/572,034

(22) PCT Filed: May 6, 2016

(86) PCT No.: PCT/US2016/031159
§ 371 (c)(1),
(2) Date: Nov. 6, 2017

(87) PCT Pub. No.: WO2016/179476
PCT Pub. Date: Nov. 10, 2016

(65) Prior Publication Data
US 2018/0135004 A1 May 17, 2018

Related U.S. Application Data

(60) Provisional application No. 62/157,638, filed on May 6, 2015.

(51) Int. Cl.
| *C07C 45/29* | (2006.01) |
| *C01B 3/00* | (2006.01) |
| *C12M 1/00* | (2006.01) |
| *C12F 3/04* | (2006.01) |
| *C12P 5/02* | (2006.01) |
| *C12P 7/64* | (2006.01) |
| *C07C 45/00* | (2006.01) |
| *C07C 29/151* | (2006.01) |
| *C10G 2/00* | (2006.01) |
| *C12M 1/107* | (2006.01) |
| *C01B 3/24* | (2006.01) |
| *C07C 1/04* | (2006.01) |
| *C12M 1/06* | (2006.01) |
| *C12M 1/02* | (2006.01) |

(52) U.S. Cl.
CPC .............. *C12M 43/00* (2013.01); *C01B 3/24* (2013.01); *C07C 1/041* (2013.01); *C07C 29/1518* (2013.01); *C07C 45/002* (2013.01); *C07C 45/29* (2013.01); *C10G 2/32* (2013.01); *C12F 3/04* (2013.01); *C12M 21/04* (2013.01); *C12M 27/02* (2013.01); *C12M 41/18* (2013.01); *C12P 5/023* (2013.01); *C12P 7/6409* (2013.01); *C12P 7/649* (2013.01); *C12P 7/6463* (2013.01); *C01B 2203/02* (2013.01); *C01B 2203/0216* (2013.01); *C01B 2203/061* (2013.01); *C01B 2203/062* (2013.01); *C10G 2300/1011* (2013.01); *Y02E 50/13* (2013.01); *Y02E 50/18* (2013.01); *Y02E 50/343* (2013.01); *Y02P 20/128* (2015.11); *Y02P 30/20* (2015.11)

(58) Field of Classification Search
CPC ........... C07C 45/29; C12M 43/00; C01B 3/24
See application file for complete search history.

(56) References Cited

U.S. PATENT DOCUMENTS

| 4,540,495 A | 9/1985 | Holloway et al. |
| 4,844,351 A | 7/1989 | Holloway |
| 4,919,813 A | 4/1990 | Weaver |
| 4,974,781 A | 12/1990 | Placzek |
| 5,157,054 A | 10/1992 | Herbolzheimer et al. |
| 5,252,613 A | 10/1993 | Chang et al. |
| 5,348,982 A | 9/1994 | Herbolzheimer et al. |
| 5,382,748 A | 1/1995 | Behrmann et al. |
| 5,445,329 A | 8/1995 | Anderson |
| 5,811,468 A | 9/1998 | Chang et al. |
| 5,866,621 A | 2/1999 | Behrmann et al. |
| 6,254,775 B1 | 7/2001 | McElvaney |
| 6,730,223 B1 | 5/2004 | Anderson et al. |
| 7,347,391 B2 | 3/2008 | Michalek et al. |
| 2002/0077373 A1 | 6/2002 | Hudson et al. |
| 2005/0064577 A1 | 3/2005 | Berzin |
| 2005/0239182 A1 | 10/2005 | Berzin |
| 2005/0260553 A1 | 11/2005 | Berzin |

(Continued)

FOREIGN PATENT DOCUMENTS

| DE | 102009014541 A1 | 9/2010 |
| EP | 2105414 A2 | 9/2009 |
| WO | 2003051803 A1 | 6/2003 |

OTHER PUBLICATIONS

Ancza et al. "Hydrodynamic Cavitation Device that Makes Straw Cuts Suitable for Efficient Biogas Production." Applied Mechanics & Materials . 2014, Issue 564, p. 572-576.

(Continued)

*Primary Examiner* — Sikarl A Witherspoon
(74) *Attorney, Agent, or Firm* — James G. Passé; Passé Intellectual Property, LLC

(57) ABSTRACT

A combined anaerobic digester system and gas-to-liquid system is disclosed. The anaerobic digester requires heat, and produces methane. The gas-to-liquid system produces heat, and converts methane to higher-value products, including methanol and formaldehyde. As such, the combination of the two systems results in significant savings in terms of capital and operating expenses. A process for producing bio-formaldehyde and bio-formalin from biogas is also disclosed.

13 Claims, No Drawings

(56) References Cited

U.S. PATENT DOCUMENTS

2009/0321349 A1 12/2009 Offerman et al.
2010/0330441 A1 12/2010 Gillespie et al.
2013/0029394 A1  1/2013 Toll et al.

OTHER PUBLICATIONS

Carlsson et al. "Controlling Selectivity in Direct Conversion of Methane into Formaldehyde/Methanol over Iron Molybdate via Periodic Operation Conditions." Energy Fuels, 2012, 26 (3), p. 1984-1987.
International Search Report and Written Opinion of International Application No. PCT/US2016/031159, dated Aug. 25, 2016 (20 pages).

COMBINED ANAEROBIC DIGESTER AND GTL SYSTEM AND METHOD OF USE THEREOF

This application claims priority of U.S. provisional application No. 62/157,638 filed on May 6, 2015, and which is incorporated in its entirety by reference.

TECHNICAL FIELD

This invention generally relates to the bioconversion of waste into useful products, and more particularly, to an anaerobic digester system and method producing a gas product, combined with a gas-to-liquid ("GTL") unit providing heat energy to the anaerobic digester system to increase the overall thermal and carbon efficiency of the bioconversion process.

BACKGROUND OF THE INVENTION

Bioconversion refers to converting organic materials (generally wastes) into useful byproducts by processes, such as fermentation, involving living organisms. Bioconversion is also generically known as anaerobic digestion (AD), which is a process commonly used for pollution control in municipal sewage treatment and livestock waste handling. Bioconversion technology can also be applied to other organic "waste" streams, which might not otherwise be "treated" or "treatable". Some examples of these types of waste are: pre- and post-consumer food waste, "green" waste (cut grass, shrub and tree trimmings, etc.), waste paper (magazines and junk mail, mixed residential, etc.), FOG wastes (fats, oils, and grease), and "high-strength" wastewaters. The organic waste can also come from industrial processes such as food processing (plant or animal), plant materials following industrial processing i.e. residues after extraction of oil.

Anaerobic digestion requires heat input in order to maximize the rate of conversion. However, known digesters do not have a ready source of heat input. Further, a typical digester is used to produce a digester gas, largely methane and carbon dioxide, which can be burned to produce electricity. In the absence of tax or other government incentives, electricity is a relatively low-value product.

It would be advantageous to provide anaerobic digesters and systems including such anaerobic digesters that can provide more valuable products than electricity, and which have a source of heat to accelerate the rate at which biomass is converted.

The present invention provides such an anaerobic digester system and overall bioconversion process.

SUMMARY OF INVENTION

In one embodiment, the present invention relates to an anaerobic digester (AD) system that comprises an anaerobic digester, which produces a mixture of methane and carbon dioxide gases, a syngas process to convert the gas mixture to a product mixture comprising carbon monoxide and hydrogen, and a gas-to-liquid reactor or series of reactors that converts the carbon monoxide and hydrogen to a product such as methanol, dimethyl ether (DME), formalin, formaldehyde, low molecular weight hydrocarbons, predominantly $C_{2-4}$ olefins, and/or paraffin wax.

In one aspect of this embodiment, the syngas process is a steam reformer, which can convert methane and water into a mixture of carbon monoxide and hydrogen where the ratio of hydrogen to carbon monoxide is around 2.5:1 to 3:1:1. For downstream conversion chemistry, a ratio of 2.2:1 can be optimal, and excess hydrogen can be used in a reverse water-gas shift reaction to convert a portion of the carbon dioxide in the gas mixture to water and carbon monoxide or used in a downstream product finishing process.

In another aspect of this embodiment, the syngas process reacts oxygen or air with methane to produce a mixture of carbon monoxide and hydrogen where the ratio of hydrogen to carbon monoxide is around 1.8:1 to 2.2:1.

In either of these aspects, a pressure swing absorption (PSA) apparatus, a membrane, or other suitable carbon dioxide removal system can be used to remove all or part of the carbon dioxide from the resulting gas mixture, as desired.

In another aspect of this embodiment, before the biomass is introduced into the digester, it is subjected to steam autoclaving, for example, by contacting the biomass with steam at an elevated temperature and pressure. This can be particularly advantageous where the source of biomass is municipal solid waste ("MSW").

Further, before the biomass is introduced into the digester, it can be subjected to rapid mixing, for example, using a cavitation mixer, such as those provided by Hydrodynamics, to further break down the organic material and feed it into the digester.

In any of these embodiments, or aspects of these embodiments, the methane from the digester is converted to a gas mixture comprising hydrogen and carbon monoxide, which is subjected to an exothermic gas-to-liquid ("GTL") process. All or part of the excess heat from the GTL process is transferred to the anaerobic digester, and as a result, the rate at which the biomass is digested will be faster than if the heat is not transferred to the digester. A portion of the heat can also be used for the optional steam autoclaving step, and heat leftover after the autoclaving step can be transferred back to the syngas process or to the GTL reactor. Alternatively, a portion of the heat can be used for biomass drying, such as drying animal feeds before they are put in storage.

Another benefit of sending heat from the GTL process to an anaerobic digester is that the use of excess heat eliminate or reduce the need for cooling radiators in the GTL plant reduces the capital cost of the GTL plant and eliminates or reduces the need for boilers or other means for providing heat to the AD. These steps reduce the capital cost and operating expense of the bioconversion process, and can also reduce the capital cost and operating expense of gas-to-liquid (GTL) process steps.

The carbon dioxide can be collected, for example, from a PSA before the GTL step, or as part of the effluent gas after the GTL step, and used to grow algae, including high-starch algae, or cyanobacteria, including mesophilic cyanobacteria or thermophilic cyanobacteria. Alternatively, all or a portion of the carbon dioxide from the AD can be incorporated into the GTL process (up to 20%) to increase the product yield. This is particularly true in the case of methanol and/or DME production.

Algae can produce oil that can be converted, via transesterification, to biodiesel. Where the GTL product is methanol, the methanol and oil can be used to produce biodiesel and glycerol, and the glycerol can optionally be added to the anaerobic digester.

Cyanobacteria produce fatty acids, and these can be converted, via esterification, to biodiesel. Where the GTL product is methanol, the methanol and fatty acids can be used to produce biodiesel and glycerol, and the glycerol can optionally be added to the anaerobic digester.

Further, the algae or cyanobacteria can be combined with other organic wastes and subjected to anaerobic digestion to further improve product yields. This is particularly true of high-starch algae, such as freshwater algae Chlorella (a highly productive source of starch).

In one embodiment, biomass remaining in the anaerobic digester can optionally be subjected to wet gasification, optionally with a dewatering step before being gasified. Wet gasification will produce additional syngas (mixture of carbon monoxide and hydrogen). This gas can be combined with the carbon monoxide and hydrogen from the conversion of the biogas (mixture of carbon dioxide and methane) from the anaerobic digester. In one aspect of this embodiment, the syngas from the wet gasification has a ratio of hydrogen to carbon monoxide of around 1:1, and can be mixed with syngas from the steam reforming of the methane in the biogas (with a ratio of hydrogen to carbon monoxide of around 3:1), to produce a syngas stream with around a 2:1 hydrogen to carbon monoxide ratio, which is ideal for several of the possible gas-to-liquid processes, including those producing methanol and paraffin wax. Lower ratios can be used where the GTL process produces low-molecular weight hydrocarbons.

Accordingly, using this process, one can maximize the use of process heat, while generating products far more valuable than electricity, and, optionally, one can use carbon dioxide (via algae or cyanobacteria production), and, optionally, glycerol (from biodiesel production), to provide far more saleable product(s) than are possible just from anaerobic digestion.

The present invention will be better understood with reference to the following Detailed Description.

DETAILED DESCRIPTION

In one embodiment, the present invention relates to an anaerobic digester (AD) system that comprises an anaerobic digester, which produces a mixture of methane and carbon dioxide gases, a gasifier, steam reformer, or other device for converting natural gas to syngas, to convert the gas mixture to a product mixture comprising carbon monoxide and hydrogen, and a gas-to-liquid reactor that converts the carbon monoxide and hydrogen to a product such as methanol, dimethyl ether (DME), low molecular weight, predominantly $C_{2-4}$ olefins, and/or paraffin wax. The anaerobic digester, gasifier, and gas-to-liquid components of the system, as well as optional components to be added to the system before biomass is digested, or after the biomass is digested, are disclosed in detail below.

The present invention will be better understood with reference to the following definitions.

1. Definitions

Certain terms are defined throughout this description as they are first used, while certain other terms used in this description are defined below:

"Aerobic digestion," as defined herein, is a process in which microorganisms break down biological material in the presence of oxygen.

"Anaerobic digestion," as defined herein, is a process in which microorganisms break down biological material in the absence of oxygen.

"Bioproducts," as defined herein, are products, such as fuel or chemical products, at least partly derived from "biomass." As used herein, biofuel encompasses hydrogen ($H_2$) and methane ($CH_4$) as well as liquid transportation fuels such as dimethyl ether, gasoline, diesel, jet, and alcohols such as methanol, ethanol, and higher alcohols.

"Biomass," as defined herein, is a renewable resource of biological origin including, but not limited to, corn stover, switchgrass, agricultural wastes, municipal solid waste, plant residues, animal renderings, and sewage. Biomass and biological residue are used interchangeably herein.

"Bioreactor," as defined herein, is a biologically active environment such as a system to grow cells.

"Photobioreactor," as defined herein, is a bioreactor with a light input. A photobioreactor typically refers to a closed system. In general, any translucent container could be a photobioreactor. For examples of photobioreactors, see Berzin, United States Published Patent Application No. 20050064577 ("Hydrogen Production with Photosynthetic Organisms and From Biodiesel Derived Therefrom"); Berzin, United States Published Patent Application No. 20050239182 ("Synthetic and Biologically-Derived Products Produced Using Biomass Produced by Photobioreactors Configured for Mitigation of Pollutants in Flue Gases"); and Berzin United States Published Patent Application No. 20050260553 ("Photobioreactor and process for Biomass Production and Mitigation of Pollutants in Flue Gases").

I. Anaerobic Digester

Anaerobic digesters are known to those of skill in the art. One example of an anaerobic digester is described in U.S. Pat. No. 6,254,775 to McElvaney.

An anaerobic digester system typically comprises a vertically upright vessel, a support matrix arranged in the vessel for supporting a microorganism biomass thereon, a vessel input for supplying an input slurry feedstock of liquid containing anaerobically digestible solids at an upper portion of the vessel above the matrix, a gas output from the upper portion of the vessel for withdrawing an output gas from the vessel generated by anaerobic digestion of the solids in the feedstock by the microorganism biomass, and an effluent output from a lower portion of the vessel for withdrawing liquid and remaining solids from the lower part of the vessel.

In one embodiment, the vessel has a height and diameter chosen to provide a ratio of 2 to 1 of liquid height to diameter in the vessel. The vessel can be formed, for example, with core, top, and base sections which are constructed of inert fiberglass-reinforced plastic. The plastic vessel sections can be coated with a translucent blue gel pigment layer which filters ambient light at wavelengths above 260 nanometers and below 700 nanometers, so as to irradiate the interior of the vessel with light of wavelength desired for cultivating the microorganism biomass.

The matrix can be formed as an array of panels mounted to a hollow spindle mounted coaxially on a central axis of the vessel. The matrix can be supported on the spindle through a plurality of wheels at spaced intervals along the vertical height of the spindle. The matrix is formed with flexible planar surfaces having a three-dimensional surface architecture. These surfaces are formed with variegated surface elements that have a large combined surface area onto which the biomass material becomes attached. A particularly advantageous material is MONSANTO® polyethylene (artificial) grass matting (manufactured without biocide), such as are typically used for entry mats. The grass matting is applied on the matrix in long sheets across the spokes of the wheels mounted to the spindle, so as to form radial panels extending from the central spindle in the vessel. The grass matting arrayed in this fashion provides a surface area to volume ratio of at least 20 to 1.

The immobilizing matrix material is selected to be relatively charge free and manufactured of material which remains uncharged when submerged in aqueous solution. Polypropylene and polyethylene are two plastic materials having polymer chains of methyl ($CH_3$) groups or hydrogen protons (H), respectively, that can be manufactured with a low surface charge characteristic. The low surface charge avoids binding other materials that will blind off the active biomass from the digestion process.

The anaerobic digester can obtain a high suspended solids digestion within the vessel by supplying liquid slurry feedstock through the vessel inlet at the upper portion of the vessel and allowing the suspended solids to flow downwardly over the biomass-supporting digester surfaces of the matrix array to the lower portion of the vessel. Recycled gas is introduced at the lower portion of the vessel to generate bubbles creating turbulence for mixing the liquid and suspended solids in the vessel. Input wastes are comminuted by a slurry grinder into a pumpable slurry. Typically, the input slurry is 8-10% by weight (80,000-100,000 mg per liter) solids, of which 90% are suspended solids of maximum particle size of 6-7 mm wide by 10-15 mm length.

A hydrolytic bacterial population is used as the biomass in order to produce exoenzymes or endoenzymes to hydrolyze solids in the feedstock. The biomass also includes fermentative bacteria for converting the hydrolysis byproducts into intermediate compounds, including acetogenic bacteria able to convert alcohols and acids into acetate, carbon dioxide and hydrogen, and methanogenic bacteria able to convert the various byproducts of the acetogens into methane. The immobilizing matrix sustains an increased density of slow growing methanogen populations in the fermentation column. The immobilized population of bacteria increase bicarbonate alkalinity sufficient to continually digest biomass with a pH as low as 4.5, especially highly acidic fruit wastes, and no artificial pH adjustments are required.

The anaerobic digesters can be used to digest sewage biosolids, low solids or screened animal manure, and low suspended solids or high soluble solids as in anaerobic filters or upflow sludge blanket digesters. The digesters can also be used to digest particulate organic wastes, especially solid wastes (the digestible fraction of municipal wastes) including pre-consumer and post-consumer food wastes, such as fats, oils and greases, food processing wastes, yard trimmings, leaves, and paper.

For feedstock preparation, input wastes can be combined with additional liquid in a mixing device (hydropulper) to form a slurry through particle size reduction. The resulting feedstock is generally limited to approximately 9% total solids (TS), due to processing equipment considerations. Once the "batch" is complete, it is loaded into the anaerobic digester with a pump, typically passing through a trash removal filter for contaminant removal.

The products of the anaerobic digester process include methane gas, carbon dioxide, leftover biomass solids, bacterial solids filtered from the liquid, and dissolved solids, and a filtrate of liquid. The gas produced typically contains approximately 65% $CH_4$, 34% $CO_2$, 0.5% $H_2S$, and the gas product is typically "scrubbed" to remove the $H_2S$.

The bacteria used to convert the biomass can be discreet cells, colonies, or aggregates of cells, cells of organisms moved to the surface by micro-diffusion of gasses, or attached cells on immobilizing matrices.

U.S. Pat. No. 4,919,813 to Weaver discloses adding photosynthetic bacteria to the fermentation to accelerate the slow step of acetate conversion to methane. These bacteria are facultative, i.e., able to grow in air or anaerobically. Their activity is enhanced by incidental light, and if light is provided (most anaerobic digesters are dark reactors), they will provide additional energy in the fermentation in the form of ATP (adenosine triphosphate). However, in one embodiment, native bacteria found in the biomass to be treated is present in the anaerobic digester, and used to digest the biomass.

The four basic stages of anaerobic digestion to produce a methane byproduct are: (1) hydrolysis of large particulate solids; (2) fermentation of large polymers into intermediates, i.e. acids and alcohols; (3) conversion of these acids and alcohols into carbon dioxide, hydrogen and small chain fatty acids, e.g. acetates; and (4) reduction of carbon dioxide, hydrogen and acetates into methane. Hydrolytic bacteria are used as the digestive biomass to produce enzymes for the breakdown of all of the various solids into smaller particles, then liquids releasing carbon dioxide and hydrogen into the fermentation liquor. The enzymes produced by the hydrolytic bacteria cleave the large polymers of cellulose, protein, and fat.

In use, the anaerobic digester process flow obtains high suspended solids digestion within the vessel in a vertically downward flow by supplying a liquid slurry feedstock from an input process through the vessel inlet at the top of the vessel to flow downwardly over the biomass-supporting digester surfaces of a matrix array. For the input process, wastes can be comminuted by the action of a slurry grinder and recirculated and processed into a pumpable slurry. Preferably, the input slurry is 8-10% by weight solids, of which 90% are suspended solids of maximum particle size of 6-7 mm wide by 10-15 mm length.

During startup of the system, a bacterial inoculum from various sludge sources is added to the biomass slurry as between 1 and 20% of the volume, more typically, around 10% of the volume. This can be sludge from wastewater sumps from animal or agricultural operations such as dairy, cattle, feeder cattle, swine, or digester sludge from municipal wastewater treatment systems. The first total volume loaded is inoculated in such a manner. For the first 30-90 days of startup, such bacterial solids residue as collected from the filter screening process can be reapplied, for example, at around a 10% rate, thereby ensuring sufficient acclimatized bacteria in the feedstock slurry. The bacteria inoculum generally has sufficient quantities of the types of bacteria needed for the bioconversion process described herein.

Gas generated by the digester process is collected, and a portion of the gas can be recycled back into the vessel to a gas diffuser as a mixing means for the slurry. Fluid from heat exchange supply can be circulated in heat exchange coils and exit to a heat exchange return. An output solids byproduct slurry can be withdrawn through a vessel outlet to an output process.

The hydrolytic bacterial population can be immobilized on a matrix, so as to have intimate contact with the feedstock, and the biomass population can produce exoenzymes or endoenzymes to hydrolyze solids in the feedstock. The type of substrate or feedstock triggers the appropriate enzyme production. As a result of hydrolysis by enzymes, these macromolecules are reduced in size, buoyancy, and weight and charge characteristics. These smaller molecules move up the hydraulic column and are further hydrolyzed by other hydrolytic bacteria. Gaseous byproducts of the various stages of digestion form as very minute micro bubbles inside the individual cell's cellular membrane and on the extracellular membrane surface and provide for movement vertically in the column acting as a natural mixing means.

The immobilizing matrix allows for increased cellular population density, producing increasing numbers of microbubbles which, aided by their proximity to each other, coalesce into larger bubbles. These larger bubbles, with increased buoyancy, move toward the surface of the column moving larger particulate and polymers with them, thereby mixing the slurry and exposing the polymers and particles to the respective sites of hydrolytic enzymatic activity, all the way toward the top of the column at the initial input level.

The feedstock digestion is performed in the anaerobic digester. This process is affected by several distinct groups of bacteria working in concert. The first group, hydrolytic bacteria, break down organic compounds to fermentation products, such as organic acids, alcohols, and $CO_2$. The second group, transitional bacteria (acetogenic, homoacetogenic), convert the products of the first group to acetate, hydrogen, and $CO_2$. These are the products which are actually converted to $CH_4$ and $CO_2$ by the third group, methanogenic bacteria. Each group relies on the next to consume its products, which prohibits inhibition that occurs when excess concentrations of these compounds are allowed to develop.

Fermentative bacteria responsible for converting the hydrolysis byproducts into intermediate compounds are capable of doubling their population biomass in less than 3 to 6 hours and will respond to substrate concentrations rapidly. As these bacteria convert intermediate products of hydrolyzed solids into alcohols and acids, the fermentation can become acidic. If the pH falls below 6 in anaerobic digesters, typically the fermentation and digestion is inhibited from going further due to the very activity of the acid producing bacteria. If present in the fermentation in high enough concentration, acetogenic bacteria are able to convert these alcohols and acids into acetate, carbon dioxide and hydrogen. This can be improved by the presence of the immobilizing matrix.

The final phase of digestion typically requires a population of methane-making organisms, methanogens, to be present and sufficiently abundant enough to convert the various byproducts of the acetogens, i.e. acetates, carbon dioxide and hydrogen into methane. Methanogens, the bacteria making up the majority of the class of archeobacteria, referred to as extremophiles, are only capable of doubling their population at a very slow rate of 192 hours. However, the various eubacteria represented by the hydrolytic, fermentative and acetogenic types of bacteria, responsible for the previous stages of digestion are able to double their respective populations 60 times faster. This difference in growth rates produces the aforementioned imbalance in cellular byproducts. This deficient rate of growth of the methanogens can be overcome by providing a matrix that enables their stable immobilization. The immobilizing matrix sustains an increased density of slow growing methanogen populations in the fermentation column.

The immobilized population of the types of bacteria responsible for complete digestion of particulate solids in the feedstock slurry are active in byproduct conversion and as a result increase the bicarbonate alkalinity, to a level approaching 10 grams per liter, thus providing sufficient natural buffer to continually digest biomass with a pH as low as 4.5, especially highly acidic fruit wastes, including the acidity resulting from rapid conversion of sugars and starches.

If the digester does not include the immobilizing matrices, then usual corrective measures available for sour digesters include dilution of the total contents of the vessel with spent digester effluent with sufficient alkalinity, or by adding basic chemicals, i.e., caustic soda, caustic lye or hydrated lime to adjust the pH artificially.

Acclimated bacteria, such as acetogens and the methanogens, can be encouraged to grow to a sufficient population density on immobilizing matrices within the liquid column such that the population of acetogens and methanogens is able to keep pace with the acid production of the fermentative organisms. Accordingly, by using immobilizing matrices for these bacteria, the need for artificial pH adjustments can be minimized or avoided altogether.

In one embodiment, the byproduct gas generated by the digester process is recycled and used as a mixing means for the slurry in the vessel. The gas can be pressurized by a low-pressure blower and delivered to the vessel contents through a gas diffuser or sparger.

Turbulent mixing produces a surface boil, often resulting in foam. This is the result in some sewage treatment anaerobic digesters where gas spargers are used as a mixing medium. Foam is considered to be a dangerous nuisance, it can fill the head space, and can eventually pass into the gas collecting header, causing the gas outlet and requiring increased maintenance. Foam can also upset the heavy floating covers of sewage digesters by flowing up and on to their tops, causing an imbalance in their position. If this happens, it can be advantageous to add a surfactant or antifoaming agent to reduce foaming, taking care not to add too much antifoam or surfactant that it is detrimental to immobilization of bacterial cells.

The anaerobic digester system can include other components, such as a storage tank to hold the input wastes to be processed, a mix tank and grinder to supply the input feedstock slurry to the digester, and a surge tank to hold liquid from the vessel effluent output passed through a screen filter to enable adding liquid to the mixing tank. An $H_2S$ scrubber can be present to removes sulfide from the output gas, particularly where the methane is to be used in a gas-to-liquid process using catalysts that are poisoned by sulfur.

A membrane separator can be present to separate the methane gas from the remainder of the gas mixture. Alternatively, a pressure swing absorption apparatus can be used to separate methane and other gases from any carbon dioxide that is present.

Carbon dioxide can be returned to the vessel for use in the spargers for generating gas turbulence for mixing in the vessel. Some of the methane gas product can be used to power generator engines to generate electricity for use in operating the system, and, optionally, to supply additional heat for the heat exchanger system.

The system is typically heated with a heat exchanger system, which includes a supply of heated fluid delivered to heater coils in the vessel. A portion of the biogas can be burned, either in a boiler or internal combustion engine, to provide heat to the digester.

The heat exchanger can be any type of heat exchanger capable of transferring process heat to another location. Examples include shell and tube heat exchangers, plate heat exchangers, plate and shell heat exchangers, adiabatic wheel heat exchangers, plate fin heat exchangers, pillow plate heat exchangers, fluid heat exchangers, waste heat recovery units, dynamic scraped surface heat exchangers, phase-change heat exchangers, direct contact heat exchangers, and microchannel heat exchangers. Helical-coil heat exchangers and spiral heat exchangers can also be used.

Effluent can be pumped over a vibrating screen to remove "coarse" solids. The screened-off solids from the output effluent can be concentrated and dried in a dryer, or, as described elsewhere herein, can be subjected to wet gasification. Where the solids are dried, they can be used as a soil additive product.

Where subjected to wet gasification, the wet output effluent can be pumped into the gasifier, eliminating the need for complex gasifier feed mechanisms and/or pelletizing of gasifier feedstock. In some cases, where total dissolved solids of effluent is less than 10-20%, a dewatering step (using vibrating screen or screw press) may be necessary before the wet effluent is pumped into the gasifier for wet gasification).

The screened effluent can be further processed with an ultrafilter. An ultrafilter is used to separate bacterial solids from the effluent liquid. These solids can be used as a plant food, and also can be added back to the mix tank to innoculate the immobilizing matrix.

The "filtrate" can be stored, or shipped to commercial users, for example, as a plant food.

The digester vessel can be constructed in a wide range of sizes and other structural materials. The biomass matrix can be formed with other structures, such as screens, vanes, racks, etc., and the immobilizer surface can be made of other suitable materials. The process parameters can vary depending on the composition of the input wastes, the processing rate or volume desired, and/or output products desired. A digester vessel may be combined with other digester vessels in an array or in stages for a wide range of bioconversion applications. It is intended that all such modifications and variations be considered as within the spirit and scope of this invention, as defined in the following claims.

II. Optional Cavitation Mixing Apparatus

Before the biomass is added to the digester, or while it is being digested, it can be subjected to rapid mixing using mechanically-induced cavitation. Suitable cavation devices are known in the art, and a representative device is described in U.S. Publication No. 20020077373 by Hudson et al. The mixture of solids in the liquid to be introduced to the anaerobic digester can be mixed together by mechanically inducing cavitation in a controlled manner. The result and goal is to obtain mixing on a microscopic level, and uniform distribution of the solid in the liquid, and this can be accomplished using controlled mechanically-induced cavitation. The result is that the rate of anaerobic digestion can be substantially increased.

A hydrosonic mixer typically includes a cylindrical housing defining an internal cylindrical chamber. The housing is typically formed of a casing capped by an end plate, which in turn is secured to the casing with bolts. The housing can also be formed in other ways, such as, for example, a central cylindrical shell capped by two end plates.

A cylindrical rotor is disposed within the cylindrical chamber of the housing and is mounted on an axially extending shaft. The shaft is journaled on either side of the rotor within bearing assemblies that, in turn, are mounted within bearing assembly housings. The bearing assembly housings are secured to the housing by means of appropriate fasteners, such as bolts. The shaft projects from one of the bearing housings for being coupled to a motive means such as an electric motor. The rotor(s) can be spun or rotated within the cylindrical chamber by activating the motor coupled to the shaft.

The rotor has a peripheral surface that is formed with one or more circumferentially extending arrays of irregularities in the form of relatively shallow holes or bores. The rotor can be provided with one, two, or more arrays of bores separated by a void, the purpose of which is described in more detail below.

Irregularities other than holes or bores also may be provided. The rotor is sized relative to the cylindrical chamber in which it is housed to define a space, referred to herein as a cavitation zone, between the peripheral surface of the rotor and the cylindrical wall of the chamber.

Inlet ports are provided in the housing for supplying fluids to be mixed to the interior chamber within the housing. Supply conduits are coupled to the inlet ports. A liquid supply conduit is coupled to the supply conduits for supplying liquid, in this case, water plus biosolids to be digested, to the hydrosonic mixer.

Where a gas is intended to be mixed with the water and the solids, a gas supply conduit can communicate with the liquid supply conduit for introducing and entraining gas in the form of bubbles within the stream of liquid flowing through the liquid supply conduit. Since the biomass is converted in an anaerobic manner, it is preferred that the gas not be oxygen, but rather, an intert gas such as nitrogen or carbon dioxide.

The term "cavitation zone" is used herein to refer to the region between the outer periphery of the rotor wherein the bores are formed and the cylindrical wall of the housing chamber. This is where the most intense cavitation activity occurs. It should be understood, however, that cavitation may occur, albeit with less intensity, in regions other than this space such as, for example, in the reservoir or region between the sides or faces of the rotor and the housing. Thus "cavitation zone" is used herein to refer to the region of most intense cavitation, but should not be interpreted as an implication that cavitation cannot occur at some level in other regions of the hydrosonic mixer.

As the mixture of solids and water moves into and through the cavitation zones, any gas bubbles in the mixture are bombarded by the microscopic cavitation bubbles as they form and further are impacted by the cavitation shock waves created as the cavitation bubbles collapse. This results in a "chopping up" of the relatively large bubbles into smaller bubbles, which themselves are chopped up into even smaller bubbles and so on in a process that occurs very quickly. Since the cavitation bubbles that cause the reduction of bubbles into ever smaller bubbles are microscopic in size, the practical lower limit to the size of the resulting air bubbles inherent in prior art mechanical mixing methods do not exist. Thus, the original bubbles are continuously chopped up and reduced to millions of tiny microscopic bubbles within the cavitation zone. The result is a total composite bubble surface area in contact with the biomass that is far greater than that possible in prior art mixing methods.

The result of the cavitation is that it creates a much larger surface area for the biomass being digested.

III. Steam Autoclaving

In some embodiments, before being added to the anaerobic digester, unsorted municipal waste can be sorted, removing the need for separate collections for recyclables, as well as waste from supermarkets, including food waste. Also, the anaerobic digester may accommodate clinical waste and animal by-products, and allow for the easy separation of clean, sterile recyclables from the biomass being digested.

Municipal solid waste ("MSW") comprises inorganic, organic and synthetic fractions. The major portion of the inorganic fraction is metal and glass containers, ceramics, masonry, building materials and the like. The organic fraction, which is typically between around 60-80 wt. % of MSW, consists of lignocellulose e.g. paper products together with yard (garden) waste and food waste. The synthetic fraction comprises plastics containers, plastics film and other synthetic plastics products. The organic fraction can be isolated from the other fractions, for example, by steam autoclaving.

One process for treating MSW is described in U.S. Pat. No. 4,540,495 to Holloway, and involves feeding MSW into a pressure vessel, subjecting it to heat at 132-160° C. (270-320° F.) under a pressure of from 276-517 kPa (40 to 75 psi) for 30-90 minutes with introduction of steam to give a residual moisture content of 60-70%. The resulting mixture is discharged and classified to give an organic fraction as fines with moisture content 60-70%.

U.S. Pat. No. 4,884,351 to Holloway discloses an autoclave for handling municipal solid waste which is in the form of a cylindrical vessel inclined at about 15° to the horizontal and having frustoconical ends each closed by a hinged hatch. The hatch at the higher end serves as inlet for the waste to be processed and that at the lower end serves as an outlet for processed waste. The autoclave is supported for rotation about its longitudinal axis and has internal flighting angled at about 30° to its axis by which in a forward rotation mode the fighting directs material to the lower end of the autoclave during filling and/or discharge and in a reverse rotation mode material being processed is conveyed upwardly and axially towards the higher end and is mixed and agitated, reverse rotation being during processing of the material. Heating is by introduction of saturated steam via an inlet on the axis of the vessel and at the upper end thereof, the processing temperature being 48-108° C. (120-228° F.) preferably 88-102° C. (190-215° F.) to rupture bags of plastics film but to leave low density plastics materials substantially intact so that they are easily identifiable and separable from other components of the waste.

U.S. Pat. No. 4,974,781 to Placzek discloses the re-pulping of re-pulpable waste material, with a water content of around 50 wt %. Waste and water is added to a rotary autoclave or so-called "trommel" to give a moisture content of at least 30% of the moisture absorptive components of the waste, 65-75% moisture content being considered an optimum. A working temperature of 100-115° C. (212-240° F.) is considered best for plastics recovery and 115-149° C. is considered best for re-pulping.

U.S. Pat. No. 5,445,329 to Anderson discloses a rotary autoclave mounted to a support frame by trunnions so that the axis of the autoclave can be tilted in either direction so that in one end of its tilting travel its forward end faces downwardly at 45° to the vertical and at the other end of its tilting travel the forward end faces upwardly at 22° to the vertical, these corresponding to loading and discharge states respectively. The vessel is supported in the frame on rotary supports provided with strain gauge based load sensors and by thrust bearings. One end of the autoclave has a door for rotation and discharge of the load, and the other end of the autoclave is provided with an external manifold from which steam can be introduced into the autoclave as it rotates by means of a hollow shaft extending cantilever-wise into the interior of the vessel for a portion of its longitudinal extent, typically 15-25% of the total length of the vessel, the shaft being provided along its length with spaced apart openings or jets through which steam can be introduced into the interior of the autoclave. The strain gauged load sensors are in the form of rollers adjacent opposed ends of the autoclave and are provided for measuring the live load distribution within the vessel. Input from the sensors is used to effect an approximately equal distribution of the material located in the vessel during the treatment operation and to control the angle of inclination of the vessel so that if a sensor associated with a front vessel support detects a load significantly greater than a sensor associated with a rear vessel support, the front end of the vessel is raised so as to cause the material within the vessel to move towards the rear end thereof, this forming part of a so-called "automatic balancing" operation.

U.S. Pat. No. 7,347,391 to Michalek discloses providing axial steam inlets at both ends of the vessel, where the vessel being supported so that its direction of tilt can be reversed in order to overcome the problem of load compaction.

After sterilizing waste by heat and pressure, organic matter can be separated and fermented/digested.

As disclosed in EPA 2105414, waste material, including organic and inorganic materials with the organic materials including starches, cellulose and other carbohydrates, can be treated using the following method:

(a) subjecting the waste material to increased temperature, pressure and moisture within an apparatus by introducing steam into the apparatus;

(b) increasing the temperature and pressure within the apparatus by an effective amount to cause the steam to reach a saturated state within the apparatus;

(c) rapidly reducing the pressure within the apparatus to cause the steam to become superheated;

(d) removing the material from the apparatus and passing the material through a screen to separate the material by size (e.g. passing material of size <12 mm); and (e) diluting the biomass obtained from the steam autoclaves with water and subjecting at least a portion of the diluted mixture to anaerobic digestion.

In particular, the process involves diluting at least a first portion of the material with water while agitating the resulting diluted mixture a sufficient amount and at an effective temperature to cause cellulose fibers that became twisted and tangled during processing within the apparatus to relax and straighten out or untangle. The specification explains that temperatures of between 126 and 132° C. (260-270° F.) reached within steam autoclaves have been found to enhance the characteristics of cellulose fibers separated from the biomass produced by the autoclaves. The softening point of lignin is approximately 128° C. (262° F.), so the temperatures reached within the steam autoclave cause the lignin that binds to the cellulose fibers to be softened, but are not enough to crystallize the lignin. Low melting point plastics within the biomass form into small beads that are easily separated during subsequent density and size separations so as to not be included with the cellulose fibers.

Another representative apparatus and process for treating municipal solid waste using steam autoclaving is described in U.S. Publication No. 20130029394 by Toll. Toll's method of treating waste material in a rotary autoclave comprises:

loading the waste material into a top opening of the autoclave whilst rotating the autoclave in a first direction in which screw flights within the autoclave convey the waste forwardly along a downwardly inclined body of the autoclave towards a base of the autoclave; rotating the autoclave in a second direction opposite to the first direction so as to establish a circulation of the loaded material between the upper and lower ends of the autoclave to facilitate vacuum and/or steam treatment thereof; and monitoring the load imparted by the autoclave adjacent upper and lower ends thereof during the reverse rotation, increase of the load adjacent the upper end of the autoclave providing an indication of effective load circulation.

If the load is not circulating as desired, remedial action may then be taken e.g. adding water and/or steam from the base of the autoclave, adding water and/or steam at the top of the autoclave or both.

Programmable logic control (PLC) can be used to dynamically modify the control parameters of the process to ensure that the waste is thoroughly mobilized within the autoclave and of uniform temperature throughout.

Toll teaches that hydrolysis is the controlling step in the anaerobic digestion (AD) of organic solids. The process of hydrolysis requires weeks to complete in a traditional AD process. A major disadvantage for AD of solid wastes is that the process requires large reactor capacities. Through an autoclave pre-treatment, the majority of organic solids with an appropriate combination of contact, processing temperature and processing time can be thermally hydrolysed and liquidized. Hence, the retention time for the following AD process can be significantly shortened and the digester tank size can be significantly reduced. Furthermore, the combination of thermal and mechanical degradation induced by the autoclave has the effect of vastly increasing the amount of organic material that can be digested by AD.

Another major drawback for traditional AD is the ammonia toxicity to the anaerobic micro-organisms associated with treating high protein content wastes. Thermal denaturation and/or hydrolysis of protein in an autoclave alleviate the inhibition of bacterial activity by ammonia build-up. High protein waste, such as slaughterhouse waste and animal by-product wastes, as well as food waste from supermarkets and catering establishments, as well as blood, can be treated in an autoclave and passed on for anaerobic digestion without unacceptable ammonia build-up.

A further major weakness for typical AD is that the process has limited tolerance to shock loadings mainly caused by uneven qualities of feedstock. Autoclaving produces a more homogenized feedstock, which significantly reduces the risks from shock loadings.

Another benefit in putting MSW through an autoclave is that the resulting material of high organic fraction and high water content can be subjected to anaerobic digestion which breaks down organic matter to produce methane gas, which is used according to the processes described herein to produce a syngas which is then converted in a GTL process. The GTL process generates waste heat, which can be used to produce all or part of the steam for the autoclaves, for example, via waste heat recovery boilers. In addition, surplus heat can be used for other purposes, such as providing heat energy to the anaerobic digesters.

Processing the organic materials in the autoclave results in them breaking down much more quickly in the anaerobic digester; the lignin (a complex chemical compound) in the organic matter starts to break down, so more gas is produced more quickly. The gas yield can be double that form non-autoclaved waste; furthermore, the peak gas flow rate can be produced in four days rather than four weeks.

Autoclaving at an appropriate temperature and for an appropriate time can also help to avoid excessive concentrations of volatile fatty acid (VFA) building up, which is an indication that anaerobic digestion is failing. As discussed above, anaerobic microorganisms used in anaerobic digestion are a mixed culture. They mainly contain three groups of bacteria: hydrolytic enzyme bacteria, acidogenic and acetogenic bacteria, and methanogenic bacteria. The hydrolytic enzyme group is responsible for hydrolysing long chain organic compounds into soluble small molecular substrates which can then be converted to VFA's by the acidogenic bacteria and eventually to acetic acid by the acetogenic bacteria. Finally the methanogenic bacteria will convert acetic acid to biogas, which mainly contains methane and carbon dioxide. When an anaerobic digester is reasonably loaded, these groups of bacteria are working in harmony. Once the loading increases, each group of bacteria will develop to reach a new balance to cope with the change of feeding rate. When the digester is overloaded, however, the metabolic balance of the different groups of anaerobic bacteria will be destroyed. The enzyme group becomes overdeveloped and development of the methanogenic bacteria will become reduced. However, the acidogenic/acetogenic bacteria are a very strong group and can carry on fast metabolism under tough circumstances as long as the temperature is maintained at a suitable level. Under these conditions a build-up of VFA's in the digester can be observed and the process failure becomes inevitable.

Autoclave pre-treatment can bring about cellular disruption which can facilitate subsequent anaerobic digestion. It can hydrolyze the majority of the cellulosic material in the waste, which can reduce the need for bacterial enzyme hydrolysis in a downstream anaerobic digestion process. When the digester is fed with autoclaved waste, the mechanism of the metabolism of the anaerobic bacteria will be automatically emphasized on the development of methanogen. Therefore, more biogas will be produced by the autoclaved materials than non-autoclaved at the same loading rates. In other words, to reach the same gas production rate, higher loading rates can be applied on the autoclaved waste than on the non-autoclaved waste. This means for treating waste streams with the same solids concentrations shorter retention time can be used on the autoclaved waste. Hence the digester volume can be reduced.

IV. Conversion of Methane to Synthesis Gas

Steam reforming of natural gas (sometimes referred to as steam methane reforming (SMR)) is the most common method of producing syngas from natural gas. At high temperatures (700-1100° C.) and in the presence of a metal-based catalyst (nickel), steam reacts with methane to yield carbon monoxide and hydrogen. These two reactions are reversible in nature.

$$CH_4 + H_2O \rightleftharpoons CO + 3H_2$$

This reaction is strongly endothermic (consumes heat).

Carbon dioxide ($CO_2$) reforming can also be used to help balance the $H_2$:CO ratio:

$$CH_4 + CO_2 = 2CO + 2H_2.$$

By adjusting the amount of steam reforming and carbon dioxide reforming, one can produce an ideal ratio of $H_2$/CO.

Where the gas including methane also includes carbon dioxide, the carbon dioxide can be converted to carbon monoxide using the reverse water-gas-shift reaction. The reaction is summarized by:

$$CO_2 + H_2 \rightleftharpoons CO + H_2O.$$

Methane can also undergo partial oxidation with molecular oxygen (at atmospheric pressure) to produce syngas, as the following equation shows:

$$2CH_4 + O_2 \rightarrow 2CO + 4H_2$$

This reaction is exothermic, and the heat given off can be used in-situ to drive the steam-methane reforming reaction. When the two processes are combined, it is referred to as autothermal reforming, and carbon dioxide can optionally be added to the gas mixtures. The high pressures and high temperatures needed for steam-reforming require a greater capital investment in equipment than is needed for a simple partial-oxidation process; however, the energy-efficiency of steam-reforming is higher than for partial-oxidation, unless the waste-heat from partial-oxidation is used.

In certain reactions, such as Fischer-Tropsch olefin synthesis, a hydrogen to carbon monoxide ratio of less than 2/1 is preferred. Accordingly, where the GTL step is an hydrocarbon synthesis step, and the syngas produced by steam reforming, partial oxidation, or autothermal reforming has too much hydrogen, the hydrogen content of the syngas can be reduced by reverse water-gas-shift, or by combining the syngas with syngas produced from biomass or coal, which tends to have around a 1/1 ratio of hydrogen to carbon monoxide. Biomass can be converted to syngas using a variety of known methods, including thermal gasification, thermal pyrolysis and steam reforming, and/or hydrogasification, each of which can produce syngas yields of 70-75% or more.

V. Gas-to-Liquid Processes

The resulting syngas can be used in methanol synthesis, Fischer-Tropsch olefin synthesis, and/or Fischer-Tropsch paraffin synthesis. The syngas can be converted to methanol or to a range of hydrocarbon products, including low molecular weight olefins or syncrude, via Fischer-Tropsch synthesis. These reactions are generally well-known in the art, and are only briefly described herein.

Methanol and Dimethyl Ether Production

Representative conditions for syngas to methanol conversion are well known and need not be described here. Briefly, carbon monoxide and hydrogen react over a catalyst to produce methanol. Today, the most widely used catalyst is a mixture of copper, zinc oxide, and alumina first used by ICI in 1966. At 5-10 MPa (50-100 atm) and 250° C., it can catalyze the production of methanol from carbon monoxide and hydrogen with high selectivity (>99.8%):

$$CO + 2H_2 \rightarrow CH_3OH$$

As discussed above, the production of synthesis gas from methane produces three moles of hydrogen gas for every mole of carbon monoxide, while the methanol synthesis consumes only two moles of hydrogen gas per mole of carbon monoxide. One way of dealing with the excess hydrogen is to inject carbon dioxide into the methanol synthesis reactor, where it, too, reacts to form methanol according to the equation:

$$CO_2 + 3H_2 \rightarrow CH_3OH + H_2O$$

On information and belief, certain catalysts synthesize methanol using $CO_2$ as an intermediary, and consuming CO only indirectly.

$$CO_2 + 3H_2 \rightarrow CH_3OH + H_2O$$

where the $H_2O$ byproduct is recycled via the water-gas shift reaction $$CO + H_2O \rightarrow CO_2 + H_2,$$

This gives an overall reaction, which is the same as listed above.

$$CO + 2H_2 \rightarrow CH_3OH.$$

In one embodiment, the methanol is further converted to dimethyl ether using appropriate catalysts and conditions, or the syngas is directly converted to dimethyl ether, both of which are well known to those of skill in the art.

There are several methods known in the art to convert syngas to DME. One option is to employ a two-step process, wherein syngas is first converted to methanol, and then the methanol is dehydrated to DME (two moles of methanol convert to one mole of DME plus one mole of water).

Typically, fixed-bed reactors are employed for the methanol synthesis and dehydration reactions, but other type reactors may be used. Catalysts for converting syngas to methanol are known, such as catalysts that include a mixture of copper, zinc oxide, and alumina. Catalysts for dehydrating methanol to DME include solid-acid catalysts, such as various forms of alumina and silica.

Another option for step (a) is to employ a one-step route, wherein syngas is directly converted, catalytically, into DME. A fixed-bed or slurry reactor may be employed, for example. Although there are potential cost and yield advantages with the one-step route, management of heat and recycle streams is regarded as more complex compared to the two-step route. Reference is made to Peng et al., "Single-Step Syngas-to-Dimethyl Ether Processes for Optimal Productivity, Minimal Emissions, and Natural Gas-Derived Syngas," Ind. Eng. Chem. Res., Vol. 38, No. 11, 1999, incorporated by reference for its teachings regarding syngas conversion to DME.

For direct synthesis, it may be desirable for the syngas to have a $H_2/CO$ ratio of about 1. In a two-step route through methanol, syngas with a $H_2/CO$ ratio of about 2 is generally preferred, for stoichiometric conversion of syngas to methanol.

Formalin/Formaldehyde Synthesis

After producing methanol, one can convert all or a portion of the methanol to formaldehyde. Formaldehyde is a gas, and can be stored under pressure, or converted to an aqueous solution of formaldehyde, known as formalin.

Any suitable methanol-to-formaldehyde synthesis can be used. In one embodiment, the reaction is carried out in a fixed bed reactor. A stream of helium and oxygen is regulated by mass flowmeters. The gas stream passes through an evaporator/saturator containing methanol. The evaporator can either be at ambient temperature or heated above ambient temperature. The temperature of the saturator can be adjusted in order to control the methanol partial pressure. The temperature of the gas mixture can be controlled by a thermocouple at the top of the saturator.

The gas mixture can subsequently be sent to a reactor, which is placed in an oven. The reaction temperature can be measured using a thermocouple which is in the catalytic bed.

The gas outlet flows can be analyzed, for example, by in-line gas chromatography using a MicroGC equipped with two columns (molecular sieve and Plot U).

The catalysts can be ground, and the fraction with a particle size of 250 microns can be mixed with a two-fold amount of silicon carbide with the same particle size and placed in the glass reactors.

The calibration of the MicroGC can be carried out with mixtures of the reference gases and the calibration for the condensable products (dimethoxymethane, methanol, methyl formate) is carried out using the evaporator/saturator.

In one example of this chemistry, 151 mg of an iron molybdate catalyst MFM3-MS (external diameter=3.9 mm, internal diameter 1.85 mm, height=4.04 mm) supplied by MAPCO can be mixed with 300 mg of silicon carbide and charged to the reactor.

The catalyst can first be activated under a helium/oxygen stream (48 Sml/min-12 Sml/min) at 340° C. for around 15 hours. Subsequently, the temperature can be brought back to 280° C. and the product can be accumulated.

The oxygen and helium flow rates can be 4.7 and 47.6 Sml/min respectively, and the concentration of the methanol can be adjusted to 5% of the reaction medium (methanol/$O_2$/inert material: 5/8.5/86.5).

Using this chemistry, a significant amount of the methanol can be converted, with a formaldehyde selectivity of around 90%. The products can be recovered at the outlet of the reactor in a thermostatically controlled cold trap. The product obtained can subsequently be passed through an anionic resin, in order to remove any acids present, and an aqueous solution of methanol can be added in order to obtain a standard formaldehyde composition with formaldehyde/water/methanol ratios adjusted as desired, for example, a weight ratio of 35/50/15. The methanol inhibits the reactions of the formaldehyde, and thus prevents the resulting formation of by-products, such as hemiacetals and polyacetals.

Thus, in one embodiment, the application relates to a process for converting biogas to methanol, and methanol to formaldehyde, forming a bio-formaldehyde. The bio-formaldehyde can be converted to bio-formalin if desired. As used herein, bio-formaldehyde is formaldehyde produced by a process which uses biogas as a feedstock, and bio-formalin is formalin produced from bio-formaldehyde.

Fischer-Tropsch Synthesis (Low MW Olefins and Paraffin Wax)

Fischer-Tropsch wax can be produced in a Fischer-Tropsch process. In Fischer-Tropsch chemistry, syngas is converted to liquid hydrocarbons by contact with a Fischer-Tropsch catalyst under reactive conditions. As discussed above, methane is gasified to provide synthesis gas. Generally, synthesis gas contains hydrogen and carbon monoxide, and may include minor amounts of carbon dioxide and/or water. The presence of sulfur, nitrogen, halogen, selenium, phosphorus and arsenic contaminants in the syngas is undesirable. For this reason and depending on the quality of the syngas, it is preferred to remove sulfur and other contaminants from the feed before performing the Fischer-Tropsch chemistry and/or methanol synthesis. Means for removing these contaminants are well known to those of skill in the art. For example, ZnO guardbeds are preferred for removing sulfur impurities. Means for removing other contaminants are well known to those of skill in the art. It also may be desirable to purify the syngas prior to the Fischer-Tropsch reactor to remove carbon dioxide produced during the syngas reaction and any additional sulfur compounds not already removed. This can be accomplished, for example, by contacting the syngas with a mildly alkaline solution (e.g., aqueous potassium carbonate) in a packed column.

In the Fischer-Tropsch process, contacting a synthesis gas comprising a mixture of $H_2$ and CO with a Fischer-Tropsch catalyst under suitable temperature and pressure reactive conditions forms liquid and gaseous hydrocarbons. The Fischer-Tropsch reaction is typically conducted at temperatures of about 300-700° F. (149-371° C.), preferably about 400-550° F. (204-228° C.); pressures of about 10-600 psia, (0.7-41 bars), preferably about 30-300 psia, (2-21 bars); and catalyst space velocities of about 100-10,000 cc/g/hr, preferably about 300-3,000 cc/g/hr. Examples of conditions for performing Fischer-Tropsch type reactions are well known to those of skill in the art.

The products of the Fischer-Tropsch synthesis process may range from $C_1$ to $C_{200+}$ with a majority in the $C_5$ to $C_{100+}$ range. The reaction can be conducted in a variety of reactor types, such as fixed bed reactors containing one or more catalyst beds, slurry reactors, fluidized bed reactors, or a combination of different type reactors. Such reaction processes and reactors are well known and documented in the literature.

The slurry Fischer-Tropsch process, which is preferred, uses superior heat (and mass) transfer characteristics for the strongly exothermic synthesis reaction and is able to produce relatively high molecular weight, paraffinic hydrocarbons when using a cobalt catalyst. In the slurry process, a syngas comprising a mixture of hydrogen and carbon monoxide is bubbled up as a third phase through a slurry which comprises a particulate Fischer-Tropsch type hydrocarbon synthesis catalyst dispersed and suspended in a slurry liquid comprising hydrocarbon products of the synthesis reaction which are liquid under the reaction conditions. The mole ratio of the hydrogen to the carbon monoxide may broadly range from about 0.5 to about 4, but is more typically within the range of from about 0.7 to about 2.75 and preferably from about 0.7 to about 2.5. A particularly preferred Fischer-Tropsch process is taught in EP 0609079, also completely incorporated herein by reference for all purposes.

In general, Fischer-Tropsch catalysts contain a Group VIII transition metal on a metal oxide support. The catalysts may also contain a noble metal promoter(s) and/or crystalline molecular sieves. Suitable Fischer-Tropsch catalysts comprise one or more of Fe, Ni, Co, Ru and Re, with cobalt being preferred. A preferred Fischer-Tropsch catalyst comprises effective amounts of cobalt and one or more of Re, Ru, Pt, Fe, Ni, Th, Zr, Hf, U, Mg and La on a suitable inorganic support material, preferably one which comprises one or more refractory metal oxides. In general, the amount of cobalt present in the catalyst is between about 1 and about 50 weight % of the total catalyst composition. The catalysts can also contain basic oxide promoters such as $ThO_2$, $La_2O_3$, MgO, and $TiO_2$, promoters such as $ZrO_2$, noble metals (Pt, Pd, Ru, Rh, Os, Ir), coinage metals (Cu, Ag, Au), and other transition metals such as Fe, Mn, Ni, and Re. Suitable support materials include alumina, silica, magnesia and titania or mixtures thereof. Preferred supports for cobalt containing catalysts comprise titania. Useful catalysts and their preparation are known and illustrated in U.S. Pat. No. 4,568,663, which is intended to be illustrative but non-limiting relative to catalyst selection.

Certain catalysts are known to provide chain growth probabilities that are relatively low to moderate, and the reaction products include a relatively high proportion of low molecular ($C_{2-8}$) weight olefins and a relatively low proportion of high molecular weight ($C_{30+}$) waxes. Certain other catalysts are known to provide relatively high chain growth probabilities, and the reaction products include a relatively low proportion of low molecular ($C_{2-8}$) weight olefins and a relatively high proportion of high molecular weight ($C_{30+}$) waxes. Such catalysts are well known to those of skill in the art and can be readily obtained and/or prepared.

The product from a Fischer-Tropsch was process contains predominantly paraffins. The products from Fischer-Tropsch reactions generally include a light reaction product and a waxy reaction product. The light reaction product (i.e., the condensate fraction) includes hydrocarbons boiling below about 700° F. (e.g. tail gases through middle distillate fuels), largely in the $C_{5-20}$ range, with decreasing amounts up to about $C_{30}$. The waxy reaction product (i.e., the wax fraction) includes hydrocarbons boiling above about 600° F. (e.g., vacuum gas oil through heavy paraffins), largely in the $C_{20+}$ range, with decreasing amounts down to $C_{10}$.

Both the light reaction product and the waxy product are substantially paraffinic. The waxy product generally comprises greater than 70 weight % normal paraffins, and often greater than 80 weight % normal paraffins. The light reaction product comprises paraffinic products with a significant proportion of alcohols and olefins. In some cases, the light reaction product may comprise as much as 50 weight %, and even higher, alcohols and olefins.

Fischer-Tropsch Olefin Chemistry

Low molecular weight olefins are typically obtained from the light gas/naphtha heavy fraction obtained via Fischer-Tropsch chemistry using iron catalysts, or other catalysts with low chain growth probabilities.

The Fischer-Tropsch reaction is typically conducted at temperatures between about 300° F. and 700° F. (149° C. to 371° C.), preferably, between about 400° F. and 550° F. (204° C. to 228° C.). The pressures are typically between about 10 and 500 psia (0.7 to 34 bars), preferably between about 30 and 300 psia (2 to 21 bars). The catalyst space velocities are typically between about from 100 and 10,000 cc/g/hr., preferably between about 300 and 3,000 cc/g/hr.

The reaction can be conducted in a variety of reactors for example, fixed bed reactors containing one or more catalyst beds, slurry reactors, fluidized bed reactors, or a combination of different type reactors. Fischer-Tropsch processes which employ particulate fluidized beds in slurry bubble column reactors are described in, for example, U.S. Pat. Nos. 5,348,982; 5,157,054; 5,252,613; 5,866,621; 5,811,468; and 5,382,748, the contents of which are hereby incorporated by reference.

Low molecular weight fractions can be obtained using conditions in which chain growth probabilities are relatively low to moderate, and the product of the reaction includes a relatively high proportion of low molecular weight ($C_{2-8}$) olefins and a relatively low proportion of high molecular weight ($C_{30+}$) waxes.

Optimized conditions for producing predominantly $C_{2-4}$ olefins are known to those of skill in the art.

Particularly good results may be obtained using residual gas recirculation. By repressing the formation of carbon dioxide by water-gas-shift reaction and increasing the $H_2$:CO utilization ratio, one can increase the proportion of carbon monoxide converted to hydrocarbons higher than methane. The catalyst may deteriorate somewhat in activity over time, and need replacement or regeneration as appropriate.

Using these conditions, one can obtain a product stream where more than half the higher hydrocarbons produced are in the $C_{2-4}$ range, with an average carbon number of around 3.3 and an olefin content of around 75 percent.

Regardless of whether the GTL step is methanol production, olefin production, or paraffin production, the reactions are exothermic, and, using heat exchangers and appropriate piping, the excess heat can be transferred to one or more of the upstream process steps. A benefit of sending heat from the GTL process to an anaerobic digester is that the use of excess heat eliminate or reduce the need for cooling radiators in the GTL plant reduces the capital cost of the GTL plant and eliminates or reduces the need for boilers or other means for providing heat to the AD. These steps reduce the capital cost and operating expense of the AD plant. That is, the digestors are particularly useful for using low grade heat, that is, heat produced in the temperature range of around 150-180 C. Higher grade heat, typically high pressure steam, can be used in the plant to help drive syngas production processes, if such are endothermic.

Ideally, at least a portion of this excess heat is used to increase the rate of the anaerobic digestion of the biomass, though when steam autoclaving is used, a portion of the heat can be used to generate the steam used in the steam autoclaving step. When this is done, residual heat from the steam autoclaving step can be passed on to the anaerobic digester.

VI. Wet Biomass Gasification

The biomass leaving the screens from the anaerobic digester tends to be relatively wet. It can be subjected to a de-watering step to lower the water content, but that water content still tends to be too high for typical gasification. One alternative approach to further drying the biomass is to use a technique known as "wet gasification" to provide additional syngas for conversion to products, such as methanol.

Where subjected to wet gasification, the wet output effluent can be pumped into the gasifier, eliminating the need for complex gasifier feed mechanisms and/or pelletizing of gasifier feedstock. In some cases, where total dissolved solids of effluent is less than 10-20%, a dewatering step (using vibrating screen or screw press) may be necessary before the wet effluent is pumped into the gasifier for wet gasification).

Representative wet-gasification processes and systems are described, for example, in U.S. Patent Publication No. 20100330441 by Gillespie. The process uses a wet devolitization reaction in lieu of a dry devolitization reaction. This increases the efficiency of the process by eliminating the energy used to drive off water, and subsequently, the energy required to create steam for injection with the gasification process.

In the Gillespie process, a biomass slurry is created from the effluent of the anaerobic digester that includes between 40% and 80% water. The feedstock slurry is devolitized at between 300 and 900 psi and between 300 and 600° F. for between 5 and 30 minutes to generate char slurry and an exhaust gas (produced from the hydrogen and oxygen present in the biomass that was converted to char). The char slurry comprises char and between 40% and 80% water. The char slurry is gasified, using suitable pressures and temperatures, to generate a product gas. The exhaust gas can be burned to provide heat energy for one or more of the process steps described herein.

In one embodiment, the exhaust gas is used to pre-heat the feedstock slurry before it is devolatilized, to provide heat for the devolitization reactor, and/or to provide heat to the gasifier used to gasify the char slurry.

Biochar has been gasified in a number of gasifiers, which are routine in the art and need not be described further here. Typically, the biochar, which includes predominantly carbon, is gasified with air, oxygen, or steam, producing a synthesis gas. This gas can be combined with the synthesis gas produced from the methane from the anaerobic digestion step, as discussed above, to provide a suitable hydrogen to carbon monoxide ratio, or, if desired, subjected to water-gas-shift to provide a suitable ratio.

VII. Carbon Dioxide Conversion to Algae or Cyanobacteria

One by-product of the anaerobic digestion processes is carbon dioxide ($CO_2$). Carbon dioxide, water and sunlight can be used to produce algae and/or cyanobacteria. Algae contain oil that can be converted into a biofuel.

In order to generate algae to be used as a biofuels feedstock, the algae can be grown in multiple different types of environments, as long as the above components are present. Algae and/or cyanobacteria can be grown in an open environment such as a tank or pond. Alternatively, algae and/or cyanobacteria can be grown in a closed environment such as a photobioreactor. Where a photobioreactor is used, inputs of light, water, and carbon dioxide are provided for the algae to grow.

Some algae are a source of triglycerides which can be extracted from the algae. The triglycerides can then be converted into a biofuel, for example, by transesterification with an alcohol such as methanol. Where the syngas generated in other steps described in the overall process is converted to methanol, the system provides the triglycerides and methanol necessary to produce biodiesel. Alternatively, the triglycerides can be hydrolyzed to provide fatty acids, which can be decarboxylated or hydrotreated to provide linear hydrocarbons, which can be subjected to further process steps, such as isomerization, hydrocracking, hydrotreating, and the like, to provide transportation fuels.

After the extraction of the triglycerides from the algae, the remaining algae biomass residue contains sugars and proteins. These can be added to the anaerobic digester to increase yields. Further, if biodiesel is produced, the crude glycerol by-product can be added to the anaerobic digester, particularly if the pH is too high, as the crude glycerol fraction, without further purification, also includes the sodium methylate catalyst used in the biodiesel step.

In use, biological residue is converted into methane and carbon dioxide via anaerobic digestion in an anaerobic digester, the methane is converted to synthesis gas which is then converted to liquid products in a GTL process step, and the carbon dioxide produced from the anaerobic digestion is used as a feedstock to grow algae and/or cyanobacteria.

The carbon dioxide, light, and water are supplied to a photobioreactor or other suitable reactor to grow algae and/or cyanobacteria.

In some embodiments, under the correct conditions, the algae may produce hydrogen. In this case, the hydrogen would be considered a biofuel.

In some embodiments, the algae is a high-starch algae, such as freshwater algae Chlorella (a highly productive source of starch), and these can be particularly preferable for anaerobic digestion, as the starch is a good feedstock for one or more of the bacteria. One such high-starch algae is disclosed in Branyikova et al. Biotechnol Bioeng. 2011 April; 108(4):766-76.

The cyanobacteria can be any type of cyanobacteria, including mesophilic cyanobacteria or thermophilic cyanobacteria. Cyanobacteria produce fatty acids, and these can be converted, via esterification, to biodiesel. Where the GTL product is methanol, the methanol and fatty acids can be used to produce biodiesel and glycerol, and the glycerol can optionally be added to the anaerobic digester.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

The invention claimed is:

1. A system for producing bioproducts, comprising an anaerobic digester that converts biomass to a mixture of gases comprising methane and carbon dioxide, coupled with a syngas generator capable of converting the methane to a mixture of carbon monoxide and hydrogen, and a gas-to-liquid reactor capable of converting the carbon monoxide and hydrogen to hydrocarbon products selected from the group consisting of alcohols, formaldehyde, formalin, low molecular weight ($C_{2-5}$) olefins and paraffins, and $C_{20-50}$ paraffins, further comprising heat exchangers to transport heat produced in the gas-to-liquid reactor to the anaerobic digester, wherein the syngas generator is an autothermal reformer or a steam reformer.

2. The system of claim 1, further comprising a steam autoclave unit adapted to receive biomass, autoclave the biomass, and transport the biomass to the anaerobic digester.

3. The system of claim 1, further comprising a cavitation stirrer adapted to receive biomass, and stir the biomass at extremely high speeds, under cavitation.

4. The system of claim 1, further comprising a pressure swing absorption unit to remove carbon dioxide from the mixture of gases produced by the anaerobic digester.

5. The system of claim 1, further comprising a reactor for growing algae or cyanobacteria, wherein the reactor is adapted to receive carbon dioxide from the anaerobic digester and/or the gas-to-liquid reactor.

6. The system of claim 1, wherein the gas-to-liquid reactor comprises a catalyst suitable for converting a mixture of carbon monoxide and hydrogen to methanol, dimethyl ether, low molecular weight ($C_{2-5}$) olefins and paraffins, or $C_{20-50}$ paraffins.

7. The system of claim 1, wherein the product is methanol, and wherein the system further comprises a reactor and catalyst for converting the methanol to formaldehyde.

8. The system of claim 5, further comprising a reactor for recovering oils from the algae.

9. The system of claim 8, further comprising a reactor for converting oils produced by algae, or fatty acids produced by cyanobacteria, to biodiesel fuel.

10. A method for producing bio-formaldehyde, comprising the steps of:
 a) converting biogas to syngas,
 b) converting the syngas to methanol, and
 c) converting the methanol to formaldehyde wherein the methanol is formed using the system of claim 1.

11. The method of claim 10, wherein the biogas is derived, in whole or in part, from the anaerobic digestion of animal waste.

12. The method of claim 11, wherein the process for producing methanol is exothermic, further comprising the step of transferring excess heat energy from the exothermic methanol producing step to an anaerobic digester, which anaerobic digester performs the anaerobic digestion of the animal waste.

13. The method of claim 10, further comprising converting all or part of the bio-formaldehyde to bio-formalin.

* * * * *